United States Patent

Garoche et al.

[11] Patent Number: 5,112,360
[45] Date of Patent: May 12, 1992

[54] PROCESSES FOR DYEING KERATINOUS FIBRES BASED ON 5,6 DIHYDROXYINDOLE OR AN INDOLE DERIVATIVE AND AT LEAST ONE RARE EARTH SALT AND COMPOSITIONS FOR IMPLEMENTATION THEREOF

[75] Inventors: Didier Garoche, Levallois-Perret; Jean F. Grollier, Paris, both of France

[73] Assignee: L'Oreal, Paris, France

[21] Appl. No.: 369,344

[22] Filed: Jun. 21, 1989

[30] Foreign Application Priority Data

Jun. 21, 1988 [LU] Luxembourg .................... 87256

[51] Int. Cl.⁵ ............................................... A61K 7/13
[52] U.S. Cl. .......................................... 8/406; 8/424; 8/405; 8/423
[58] Field of Search ................ 8/423, 421, 406, 405, 8/424, 426, 634, 404

[56] References Cited

U.S. PATENT DOCUMENTS

| | | | |
|---|---|---|---|
| 4,804,385 | 2/1989 | Grollier et al. | 8/423 |
| 4,808,190 | 2/1989 | Grollier et al. | 8/423 |
| 4,822,375 | 4/1989 | Lang et al. | 8/423 |
| 4,992,077 | 2/1991 | Tennigkeit et al. | 8/406 |

FOREIGN PATENT DOCUMENTS

| | | |
|---|---|---|
| 0271186 | 10/1987 | European Pat. Off. . |
| 3701044 | 1/1987 | Fed. Rep. of Germany . |
| 2327761 | 10/1976 | France . |
| 8801162 | 2/1988 | PCT Int'l Appl. . |
| 2132642 | 7/1984 | United Kingdom . |
| 2207443 | 7/1988 | United Kingdom . |

Primary Examiner—Prince Willis, Jr.
Assistant Examiner—J. Silbermann
Attorney, Agent, or Firm—Cushman, Darby & Cushman

[57] ABSTRACT

Process for dyeing keratinous fibres, comprising the application of:
(a) a component (A) containing at least one rare earth salt in a medium suitable for dyeing, and
(b) a component (b) containing, in a medium suitable for dyeing, at least one indole derivative of formula (I):

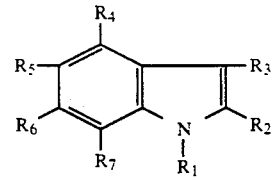

in which:

$R_1$ denotes a hydrogen atom or a $C_1-C_4$ alkyl group;

$R_2$ and $R_3$, which may be identical or different, denote a hydrogen atom, a $C_1-C_4$-alkyl group, a carboxyl group or a $(C_1-C_4$ alkoxy)carbonyl group;

$R_4$, $R_5$, $R_6$ and $R_7$, which may be identical or different, denote a hydrogen atom, a $C_1-C_4$ alkyl, carboxyl, $C_1-C_4$ carboxyalkyl, $(C_1-C_4$ alkoxy) carbonyl, $(C_1-C_4$ alkoxy)carbonyl($C_1-C_4$ alkyl), carbamyl, halogen, mono- or polyhydroxy($C_1-C_4$ alkyl) or $C_1-C_4$ aminoalkyl radical, a group OZ in which Z denotes hydrogen or $C_1-C_{20}$ linear or branched alkyl, an aryl($C_1-C_4$ alkyl) group, a formyl group, a linear or branched $C_2-C_{20}$ acyl group, a linear or branched $C_3-C_{20}$ alkenoyl group, a group $-SiR_{11}R_{12}R_{13}$, a group $-P(O)(OR_8)_2$ or a group $R_6OSO_2-$; it being possible for the radicals $R_4$ and $R_5$, or alternatively $R_5$ and $R_6$, or alternatively $R_6$ and $R_7$ to form, together with the carbon atoms to which they are attached, a ring optionally containing a carbonyl group, a thiocarbonyl group, a group $>P(O)(OR_8)$ or a group $>CR_9R_{10}$;

with the proviso that at least one of the radicals $R_4$ to $R_7$ denotes a group OZ or alternatively that $R_4$ and $R_5$, or alternatively $R_5$ and $R_6$, or alternatively $R_6$ and $R_7$ form a ring, $R_8$ and $R_9$ denote a hydrogen atom or a $C_1-C_4$ lower alkyl group, $R_{10}$ denotes a $C_1-C_4$ alkoxy group or a mono- or di($C_1-C_4$ alkyl)amino group, and $R_{11}$, $R_{12}$ and $R_{13}$, which may be identical or different, denote linear or branched $C_1-C_4$ alkyl groups, and the corresponding salts of alkali metals and alkaline-earth metals, ammonium salts and amine salts, or the addition salts of inorganic or organic acids.

the components (A) and (B) being applied on the fibres using a single composition, or the component (A) being applied on the fibres prior or subsequent to the application of the component (B).

29 Claims, No Drawings

PROCESSES FOR DYEING KERATINOUS FIBRES BASED ON 5,6 DIHYDROXYINDOLE OR AN INDOLE DERIVATIVE AND AT LEAST ONE RARE EARTH SALT AND COMPOSITIONS FOR IMPLEMENTATION THEREOF

The present invention relates to new processes for dyeing keratinous fibres, and especially human hair, based on 5,6-dihydroxyindole and/or an indole derivative and at least one rare earth salt, and to the compositions used in these processes.

The natural biosynthesis of eumelanins or insoluble black pigments is accomplished in several stages by polymerization of the oxidation products of an amino acid:tyrosine. One of these oxidation products is 5,6-dihydroxyindole, which is oxidized in turn to eumelanin.

It is well known to dye human keratinous fibres with 5,6-dihydroxyindole, in particular by processes which employ metal salts of groups III to VIII of the Periodic Table and especially a cupric salt. These salts accelerate the process of oxidative polymerization of the indole derivative.

The metal salts are generally applied in a separate stage from that of the application of the 5,6-dihydroxyindole-based composition.

These processes of the prior art propose the production of intense black dyeing in short times using cupric salts, it being possible to obtain the range of light or intermediate shades preceding black only in a subsequent stage, by lightening the black by means of hydrogen peroxide solution.

These same processes of the prior art reveal that the metallic promoters mentioned above enable dyeing to be obtained in more or less dark shades of grey, without it being possible to increase the depth of the color obtained by a longer exposure of the hair to the dye or higher concentrations of the metallic promoter.

The applicants have discovered that, in contrast to what was possible with the metal salts used in the prior art, and more especially a cupric salt, hair could be progressively dyed directly in light or more or less dark shades and with the possibility of obtaining intense blacks if so desired, the light and intermediate shades being obtained without the need to resort to a subsequent additional stage of lightening with hydrogen peroxide.

Such a dyeing is possible as a result of the use of rare earth salts, employed either in the context of a pretreatment or post-treatment before or after the application of the composition based on 5,6-dihydroxyindole and/or an indole derivative, or in the same composition.

Moreover, as a result of the combination with rare earth salts used according to the invention, a uniform initial coloring of the hair is obtained after the conventional treatments subsequent to dyeing, such as bleaching, this not being possible with the cupric, ferrous or manganese salts of the prior art.

The dyeing thereby obtained has, moreover, the advantage, even when subjected, in particular, to damaging environmental agents (the sun's rays, adverse weather, and the like) and to shampooing, of being especially homogeneous without exhibiting the undesirable glints which are observed with corresponding colorations obtained with cupric, ferrous or manganese salts, which can give rise to reversion to heterogeneous colors and/or to a color change towards greenish, bluish-green or orange colors.

Moreover, the hair is less degraded as a result of the use of rare earth salts, in particular cerium salts, and have a softer feel.

The process and the compositions according to the invention even enable stronger colorations to be obtained, compared with compositions of the prior art not employing metal salts.

A subject of the invention hence consists of processes for dyeing keratinous fibres, and especially human hair, employing, in separate stages, a composition containing a rare earth salt and the application of a composition containing an indole derivative of the formula (I) defined below.

Another subject of the invention consists of a process for dyeing keratinous fibres, and especially human hair, employing, in a single stage, a composition containing both a rare earth salt and an indole derivative of the formula (I) defined below.

Another subject of the invention consists of the compositions employed in the context of this process.

Another subject of the invention consists of a multi-compartment device or kit intended for use in the employment of the processes and compositions according to the invention.

Other subjects of the invention will become apparent on reading the description and examples which follow.

The process for dyeing keratinous fibres, and especially human hair, according to the invention is essentially characterized in that it comprises the use of:

(a) a component (A) containing at least one rare earth salt in a medium suitable for dyeing, and (b) a component (B) containing, in a medium suitable for dyeing, at least one indole derivative of formula (I):

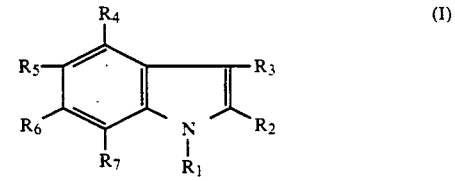

in which:

$R_1$ denotes a hydrogen atom or a $C_1$-$C_4$ alkyl group;

$R_2$ and $R_3$, which may be identical or different, denote a hydrogen atom, a $C_1$-$C_4$-alkyl group, a carboxyl group or a ($C_1$-$C_4$ alkoxy)carbonyl group;

$R_4$, $R_5$, $R_6$ and $R_7$, which may be identical or different, denote a hydrogen atom, a $C_1$-$C_4$ alkyl, carboxyl, $C_1$-$C_4$ carboxyalkyl, ($C_1$-$C_4$ alkoxy)carbonyl, ($C_1$-$C_4$ alkoxy)carbonyl($C_1$-$C_4$ alkyl), carbamyl, halogen, mono- or polyhydroxy($C_1$-$C_4$ alkyl) or $C_1$-$C_4$ aminoalkyl radical, a group OZ in which Z denotes hydrogen or $C_1$-$C_{20}$ linear or branched a an aryl($C_1$-$C_4$ alkyl) group, a formyl group, a linear or branched $C_2$-$C_{20}$ acyl group, a linear or branched $C_3$-$C_{20}$ alkenoyl group, a group —$SiR_{11}R_{12}R_{13}$, a group —$P(O)(OR_8)_2$ or a group $R_8OSO_2$—; it being possible for the radicals $R_4$ and $R_5$, or alternatively $R_5$ and $R_6$, or alternatively $R_6$ and $R_7$ to form, together with the carbon atoms to which they are attached, a ring optionally containing a carbonyl group, a thiocarbonyl group, a group >$P(O)(OR_8)$ or a group >$CR_9R_{10}$;

with the proviso that at least one of the radicals $R_4$ to $R_7$ denotes a group OZ or alternatively that $R_4$ and $R_5$, or alternatively $R_5$ and $R_6$, or alternatively $R_6$ and $R_7$ form a ring, $R_8$ and $R_9$ denote a hydrogen atom or a $C_1-C_4$ lower alkyl group, $R_{10}$ denotes a $C_1-C_4$ alkoxy group or a mono- or di($C_1-C_4$ alkyl)amino group, and $R_{11}$, $R_{12}$ and $R_{13}$, which may be identical or different, denote linear or branched $C_1-C_4$ alkyl groups, and the corresponding salts of alkali metals and alkaline-earth metals, ammonium salts and amine salts, or the addition salts with inorganic or organic acids, the components (A) and (B) being either applied on the fibres using a single composition, or alternatively the component (A) being applied on the fibres prior or subsequent to the application of the component (B).

Preferred indole derivatives of formula (I) are chosen from 5,6-dihydroxyindole, 4-hydroxy-5-methoxyindole, 5-methoxy-6-hydroxyindole, 2,3-dimethyl-5,6-dihydroxyindole, 3-methyl-5,6-dihydroxyindole and 6-hydroxyindole.

An especially preferred indole derivative is 5,6-dihydroxyindole, which may be used alone or mixed with the other indole derivatives of formula (I) defined above.

The prefered salts of the indole derivatives of formula (I) are hydrochlorides or hydrobromides.

The rare earth salts used according to the invention are, more especially, chosen from salts of lanthanides, and in particular from salts of cerium $Ce^{3+}$, $Ce^{4+}$; of lanthanum $La^{3+}$; of europium $Eu^{2+}$, $Eu^{3+}$; of gadolinium $Gd^{3+}$; of ytterbium $Yb^{2+}$, $Yb^{3+}$; and of dysprosium $Dy^{3+}$. Preferred salts are, in particular, the sulphates, chlorides or nitrates.

Especially preferred salts are the salts of cerium $Ce^{3+}$ and $Ce^{4+}$ in the form of sulphates and chlorides.

In the context of the single-stage process in which the rare earth salt and the indole derivative of formula (I) defined above are present together, preferred salts are those of cerium $Ce^{3+}$, europium $Eu^{2+}$ and ytterbium $Yb^{2+}$ in the form of sulphates and chlorides.

A first embodiment of the invention consists in applying on the keratinous fibres, in a first stage, the component (A) in the form of a composition containing at least one rare earth salt, as defined above, in a medium suitable for dyeing.

The application of this first composition is followed, after an exposure time of between 1 and 30 minutes, and preferably between 5 and 20 minutes, by the application of the component (B), consisting of a composition containing the indole derivative of formula (I) defined above in a medium suitable for dyeing.

An especially preferred embodiment consists in applying, in the first stage, by way of rare earth salts, especially when the composition is applied on human hair, a salt of cerium $Ce^{3+}$ or $Ce^{4+}$, and preferably a $Ce^{3+}$ salt, in an aqueous medium suitable for dyeing having a pH of between 2 and 12.

The hair thus treated may be rinsed with water.

The composition based on an indole derivative, applied in the second stage, preferably has a pH of between 7.5 and 12, and more especially between 8 and 11. It is maintained in contact with the fibres for an exposure time of between 1 and 30 minutes, and preferably between 5 and 20 minutes.

This treatment can optionally be followed by a treatment with hydrogen peroxide using a composition having a pH of between 2 and 12, or alternatively by a treatment with an inorganic or organic base.

According to another embodiment of the invention, the hair may be dyed using a single composition containing the component (A) defined above and the component (B). Such a composition can optionally be prepared at the requisite time just before use.

Especially preferred compositions of this type are compositions containing, by way of rare earth salts, cerium in the form of $Ce^{3+}$ or $Ce^{4+}$, and especially a $Ce^{3+}$ salt, in combination with the indole derivative of formula (I) in a medium suitable for dyeing, at a pH of between 2 and 7, and more especially between 3 and 6. The exposure time is similar to that stated above.

The ready-for-use compositions containing the $Ce^{3+}$ salt in combination with an indole derivative of formula (I) in a medium suitable for dyeing, at a pH of between 2 and 7, are especially stable with respect to time.

The application of this composition can optionally be followed by a treatment with hydrogen peroxide using a composition having a pH of between 2 and 12, or by a treatment with an inorganic or organic base.

The inorganic or organic bases are chosen, more especially, from sodium hydroxide, potassium hydroxide, ammonia solution and mono- and triethanolamines.

The rare earth salts are present in the compositions used according to the invention in proportions preferably of between 0.1 and 8% by weight, relative to the total weight of the composition containing the rare earth salt and indole derivative of formula (I) applied to the fibres. This proportion is preferably between 0.5 and 5% in the component (A).

The indole derivative(s) of formula (I) is preferably present in proportions of between 0.1 and 5% by weight, and especially between 0.1 and 3% by weight, relative to the total weight of the composition applied on the fibres. This proportion is preferably between 0.1 and 5% in the component (B).

The medium suitable for dyeing, used in the components A) and (B), is preferably an aqueous medium consisting of water or a mixture of water and an organic solvent which is acceptable from the cosmetic standpoint, when the composition is intended for use in the dyeing of human keratinous fibres.

The solvents which are usable in these compositions are preferably chosen from $C_1-C_4$ lower alcohols, more especially ethyl alcohol, propyl or isopropyl alcohol and tert-butyl alcohol, alkylene glycols such as ethylene glycol and propylene glycol, alkylene glycol alkyl ethers such as ethylene glycol monomethyl, monoethyl and monobutyl ethers and propylene glycol and dipropylene glycol monomethyl ethers, and methyl lactate.

Especially preferred solvents are ethyl alcohol and propylene glycol.

The compositions containing the indole derivative(s) of formula (I) may be stored in an anhydrous solvent medium preferably chosen from the solvents stated above. An anhydrous solvent denotes a solvent containing less than 1% of water.

These compositions are intended for mixing immediately before use with an aqueous medium suitable for dyeing, as defined above, or they can also be applied directly on wet hair during the dyeing process.

The compositions used according to the invention can contain any other adjuvants customarily used in the dyeing of keratinous fibres, and more especially cosmetically acceptable adjuvants when these compositions are applied for dyeing living human hair.

In the latter case, the compositions can contain, in particular, fatty amides in proportions of 0.05 to 10% by weight, anionic, cationic, nonionic or amphoteric surfactants or mixtures thereof, preferably present in proportions of between 0.1 and 50% by weight, thickening agents, perfumes, sequestering agents, film-forming agents, dispersants, conditioners, preservatives, opacifiers and agents for swelling keratinous fibres.

The thickeners are more especially chosen from sodium alginate, gum arabic, guar gum, heterobiopolysaccharides such as xanthan gum or scleroglucans, cellulose derivatives such as methylcellulose, hydroxyethylcellulose, hydroxypropylmethylcellulose and the sodium salt of carboxym-ethylcellulose, and acrylic acid polymers, preferably crosslinked.

It is also possible to use inorganic thickening agents such as bentonite. These thickeners are used alone or mixed, and are preferably present in proportions of between 0.1 and 5% by weight relative to the total weight of the composition, and advantageously between 0.5 and 3% by weight.

The alkalinizing agents which are usable in the compositions used according to the invention can be, in particular, amines such as alkanolamines, alkylamines and alkali metal or ammonium hydroxides or carbonates. The acidifying agents which are usable in the compositions according to the invention may be chosen from lactic acid, acetic acid, tartaric acid, phosphoric acid, hydrochloric acid and citric acid. It is naturally possible to use any other alkalinizing or acidifying agent which is acceptable, in particular in the case of hair dyeing, in cosmetics.

The composition containing the indole derivative(s) of formula (I), combined or otherwise with the rare earth salt, may be used, in one embodiment of the invention, in the form of an aerosol foam. It is packaged in this case under pressure in an aerosol device in the presence of a propellent agent and at least one foam generator. Foam-generating agents are, more especially, anionic, cationic, nonionic or amphoteric foaming polymers, or mixtures thereof, or surfactants of the type defined above.

An embodiment of the invention consists of a composition based on an indole derivative of formula (I) and a rare earth salt in a medium suitable for dyeing, containing at least one foam-generating agent, packaged in an aerosol device in the presence of a propellant agent.

The applicants have found, in particular, that the foam produced by expansion in the air on emergence from the aerosol device is uncolored, and that it rapidly dyes hair black or in different gradations of grey after an exposure time of 1 to 20 minutes, and especially 1 to 15 minutes.

The indole derivative(s) of formula (I) combined with rare earth salts such as $Ce^{3+}$, $Eu^{2+}$ and $Yb^{2+}$ can also be stored in a closed vessel essentially free from oxygen, in the presence of a non-oxidizing inert gas such as nitrogen, carbon dioxide and the like.

In another implementation of the process according to the invention, the composition containing the indole derivative (s) of formula (I) on the one hand, and that containing the rare earth salt on the other hand, may be packaged in multi-department devices, also known as dyeing kits or outfits, containing all the components intended for application for an individual dyeing on keratinous fibres, in the successive applications with or without premixing.

Such a device comprises a first compartment containing at least one rare earth salt in a medium suitable for dyeing, a second compartment comprising a composition containing at least the indole derivative of formula (I) in a medium suitable for dyeing, and optionally a third compartment containing an aqueous medium suitable for dyeing and intended for mixing with the contents of the second compartment when the composition containing the indole derivative is anhydrous.

An especially suitable device for preparing the mixture at the time of use is represented by a distributor assembly of the type described in French Patent 2,586,913, comprising two separate bags combined in a flexible case. One of the two bags contains at least the indole derivative in a medium suitable for dyeing, and the other at least the rare earth salt in a medium suitable for dyeing, defined above.

The especially preferred application of the process and the compositions according to the invention is the dyeing of human keratinous fibres, and especially living human hair.

The applicants found, moreover, that it was possible to use these compositions for dyeing furs or wool.

The examples which follow are designed to illustrate the invention, no limitation of the latter being implied.

EXAMPLE 1

The dyeing of naturally grey hair containing 90% of white fibres is performed by applying successively two compositions (A) and (B) and performing an intermediate rinsing between the two applications.

| Composition (A) | |
| --- | --- |
| $Ce_2(SO_4)_3.5H_2O$ | 2.6 g |
| Sodium lauryl ether sulphate oxyethylenated with 2 moles of ethylene oxide, expressed as g AS | 0.9 g AS |
| Citric acid qs pH 5 | |
| Water qs | 100.0 g |
| Composition (B) | |
| 5,6-Dihydroxyindole | 1.0 g |
| Ethyl alcohol | 10.0 g |
| Sodium lauryl ether sulphate oxyethylenated with 2 moles of ethylene oxide, expressed as g AS | 0.9 g AS |
| NaOH qs pH 9.5 | |
| Water qs | 100.0 g |

The rare earth salt composition (A) is applied on the hair and left in place for 10 minutes. After rinsing the hair with water, the 5,6-dihydroxyindole composition is applied and left in place for 10 minutes. After rinsing with water and shampooing, the hair is dyed a very dark grey.

EXAMPLE 2

The procedure is as in Example 1, using a $Ce_2(SO_4)_3.5H_2O$ composition at a pH adjusted to 9.5 with monoethanolamine instead of 5. A dark grey coloration is obtained.

EXAMPLE 3

The procedure is as in Example 1, using 1.5 g of $Ce(SO_4)_3.3H_2O$ instead of 2 6 g of $Ce_2(SO_4)_3.5H_2O$. A medium grey-brown coloration is obtained.

EXAMPLE 4

The procedure is as in Example 3, using a $Ce(SO_4)_2.3H_2O$ composition at a pH adjusted to 9.5 with monoethanolamine instead of 5. A slightly stronger medium grey-brown coloration than in Example 3 is obtained.

EXAMPLE 5

The dyeing of naturally grey hair containing 90% of white fibres is performed by applying a composition containing:

| | |
|---|---|
| 5,6-Dihydroxyindole | 1.0 g |
| $Ce_2(SO_4)_3.5H_2O$ | 2.6 g |
| Ethyl alcohol | 10.0 g |
| Sodium lauryl ether sulphate oxyethylenated with 2 moles of ethylene oxide, expressed as g AS | 0.9 g AS |
| Citric acid qs pH 5 | |
| Water qs | 100.0 g |

The above composition is applied on the hair and left in place for 10 minutes. After rinsing with water and shampooing, a light brown shade is obtained. After three successive applications of this composition, a dark brown shade is obtained.

EXAMPLE 6

The dyeing of naturally grey hair containing 90% of white fibres is performed by means of the following composition, packaged as a kit, which is prepared at the time of use by mixing two compositions (A) and (B).

| | |
|---|---|
| Composition (A) | |
| $Ce(SO_4)_2.3H_2O$ | 3.0 g |
| Sodium lauryl ether sulphate oxyethylenated with 2 moles of ethylene oxide, expressed as g AS | 1.8 g AS |
| Citric acid qs pH 5 | |
| Water qs | 100.0 g |
| Composition (B) | |
| 5,6-Dihydroxyindole | 2.0 g |
| Ethyl alcohol | 20.0 g |
| Citric acid qs pH 5 | |
| Water qs | 100.0 g |

At the time of use, a 50:50 mixture by weight of the two compositions (A)+(B) is prepared. The resulting composition is applied on the hair for 10 minutes. The hair is rinsed with water. After shampooing, the hair is dyed brown. Four successive applications of this composition give a dark brown coloration.

EXAMPLE 7

The procedure is as in Example 6, adjusting the pH of the two compositions to 9.5 with monoethanolamine. A dark blond coloration is obtained after four successive applications of the composition.

EXAMPLE 8

On hair dyed by an application of the composition of Example 5, an oxidizing treatment lasting 10 minutes is performed with "10 volumes" aqueous hydrogen peroxide solution having a natural pH of 3.95. After rinsing with water, a dark grey coloration is obtained.

EXAMPLE 9

On hair dyed by an application of the composition of Example 6, an oxidizing treatment lasting 10 minutes is performed with a "10 volumes" hydrogen peroxide solution having a natural pH of 3.95. After rinsing with water, the hair is dyed a dark grey-brown.

EXAMPLE 10

The dyeing of 90% white naturally grey hair is performed by applying a ready-for-use composition containing:

| | |
|---|---|
| 5,6-Dihydroxyindole | 0.15 g |
| $CeCl_3.7H_2O$ | 1.0 g |
| Guar gum sold by the company CELANESE under the name JAGUAR HP 60 | 1.0 g |
| Ethyl alcohol | 10.0 g |
| Natural pH 5 | |
| Water qs | 100.0 g |

The above composition is applied on the hair and left in place for 10 minutes. After rinsing with water and drying, a medium ash-grey shade is obtained.

EXAMPLE 11

The dyeing of naturally grey hair containing 90% of white fibres is performed by means of the following composition, packaged as a kit, which is prepared at the time of use by mixing two compositions (A) and (B):

| | |
|---|---|
| Composition (A) | |
| $CeCl_3.7H_2O$ | 1.0 g |
| Citric acid qs pH 5 | |
| Water qs | 100.0 g |
| Composition (B) | |
| 5,6-Dihydroxyindole | 2.0 g |
| Ethyl alcohol | 20.0 g |
| Sodium lauryl ether sulphate oxyethylenated with 2 moles of ethylene oxide, expressed as g AS | 1.8 g AS |
| Citric acid qs pH 5 | |
| Water qs | 100.0 g |

At the time of use, the two compositions (A) and (B) are mixed in a 50:50 ratio by weight. The resulting composition is applied on the hair for 10 minutes. The hair is rinsed with water. After shampooing, the hair is dyed a dark grey.

EXAMPLE 12

The dyeing of naturally grey hair containing 90% of white fibres is performed by applying successively two compositions (B) and then (A) without performing an intermediate rinsing.

| | |
|---|---|
| Composition (A) | |
| $CeCl_3.7H_2O$ | 1.5 g |
| Sodium lauryl ether sulphate oxyethylenated with 2 moles of ethylene oxide, expressed as g AS | 0.9 g AS |
| Monoethanolamine qs pH 6 | |
| Water qs | 100.0 g |
| Composition (B) | |
| 5,6-Dihydroxyindole | 1.0 g |
| Ethyl alcohol | 10.0 g |
| Sodium lauryl ether sulphate oxyethylenated with 2 moles of ethylene oxide, expressed as g AS | 0.9 g AS |
| | 0.9 g AS |
| NaOH qs pH 9.5 | |
| Water qs | 100.0 g |

The 5,6-dihydroxyindole composition (B) is applied on the hair and left in place for 10 minutes.

The rare earth salt composition (A) is then applied and left in place for 10 minutes.

After rinsing with water and shampooing, the hair is dyed a dark grey.

EXAMPLE 13

The dyeing of 90% white naturally grey hair is performed by applying a ready-for-use composition containing:

| | |
|---|---|
| 5,6-Dihydroxyindole | 0.75 g |
| $CeCl_3.7H_2O$ | 3.7 g |
| Natural pH 4.47 | |
| Water qs | 100.0 g |

The above composition is applied on the hair and left in place for 10 minutes.

After rinsing with water and drying, a dark grey shade is obtained.

EXAMPLE 14

The dyeing of 90% white permanent-waved grey hair is performed by applying a ready-for-use composition containing:

| | |
|---|---|
| 4-Hydroxy-5-methoxyindole | 0.5 g |
| $Ce_2(SO_4)_3.5H_2O$ | 0.2 g |
| Ethyl alcohol | 16.5 g |
| Natural pH 3.9 | |
| Water qs | 100.0 g |

The above composition is applied on the hair and left in place for 10 minutes. After rinsing with water, shampooing and drying, a purple-grey shade is obtained.

EXAMPLE 15

Example 14 is repeated, following the 10 minutes' exposure to the composition by a towel-drying of the locks and the application of an alkaline aqueous NaOH solution at pH 11.9 for 10 minutes. After rinsing with water, shampooing and drying, a purple shade is obtained.

EXAMPLE 16

The dyeing of 90% white permanent-waved grey hair is performed by applying a ready-for-use composition containing:

| | |
|---|---|
| 5,6-Dihydroxyindole | 0.5 g |
| 2,3-Dimethyl-5,6-dihydroxyindole hydrobromide | 1.0 g |
| Ethyl alcohol | 10.0 g |
| Guar gum sold by the company CELANESE under the name JAGUAR HP60 | 1.0 g |
| Glycoside alkyl ether sold by the company SEPPIC at a concentration of 60% AS under the name TRITON CG 110 | 5.0 g AS |
| Preservatives qs | |
| Water qs | 80.0 g |
| pH adjusted to 7.6 with triethanolamine | |
| To this solution, 20 g of $CeCl_3.7H_2O$ in 5% strength aqueous solution is added | (equivalent to 1 g AS of $CeCl_3.7H_2O$) |

The final pH is 6.5.

The above composition is applied on the hair and left in place for 15 minutes. After rinsing with water, shampooing and drying, a slightly pearly grey shade is obtained. A further application of the composition for the same length of time gives, after rinsing with water, shampooing and drying, a dark auburn shade.

EXAMPLE 17

The dyeing of naturally grey hair containing 90% of white fibres is performed by means of the following composition, packaged as a kit, which is prepared at the time of use by mixing two compositions (A) and (B).

| | |
|---|---|
| Composition (A) | |
| $Ce(SO_4)_2.3H_2O$ | 0.8 g |
| Natural pH 2 | |
| Water qs | 100.0 g |
| Composition (B) | |
| 3-Methyl-5,6-dihydroxyindole | 4.0 g |
| Ethyl alcohol qs | 100.0 g |

At the time of use, a 50:50 mixture by weight of the two compositions (A) and (B) is prepared. The resulting composition is applied on the hair for 15 minutes. The hair is rinsed with water. After shampooing and drying, the hair is dyed uniformly grey.

EXAMPLE 18

The dyeing of permanent-waved grey hair containing 90% of white fibres is performed by applying successively two compositions (A) and (B).

| | |
|---|---|
| Composition (A) | |
| $CeCl_3.7H_2O$ | 1.0 g |
| Natural pH 5.4 | |
| Water qs | 100.0 g |
| Composition (B) | |
| 5-Methoxy-6-hydroxyindole | 1.0 g |
| Ethyl alcohol | 10.0 g |
| Natural pH 8 | |
| Water qs | 100.0 g |

The rare earth salt composition (A) is applied on the hair, and left in place for 5 minutes. After towel-drying, the composition (B) is applied and left in place for 10 minutes. After rinsing with water, shampooing and drying, the hair is dyed uniformly grey.

EXAMPLE 19

The dyeing of naturally grey hair containing 90% of white fibres is performed by applying successively two compositions (B) and then (A).

| | |
|---|---|
| Composition (A) | |
| $Ce_2(SO_4)_3.5H_2O$ | 1.25 g |
| Natural pH 2 | |
| Water qs | 100.0 g |
| Composition (B) | |
| 6-Hydroxyindole | 1.0 g |
| Ethyl alcohol | 25.0 g |
| Natural pH 6 | |
| Water qs | 100.0 g |

The indole derivative composition (B) is applied on the hair, and left in place for 10 minutes. After towel-drying, the rare earth salt composition (A) is applied and left in place for 10 minutes. After rinsing with water, shampooing and drying, the hair is dyed uniformly a light pearly grey.

EXAMPLE 20

The dyeing of naturally grey hair containing 90% of white fibres is performed by applying successively two

| Composition (A) | |
|---|---|
| Ce$_2$(SO$_4$)$_3$.5H$_2$O | 1.5 g |
| Natural pH 2 | |
| Water qs | 100.0 g |
| Composition (B) | |
| 6-Hydroxyindole | 1.0 g |
| 5,6-Dihydroxyindole | 0.7 g |
| Ethyl alcohol | 16.5 g |
| Natural pH 7.2 | |
| Water qs | 100.0 g |

The indole derivative composition (B) is applied on the hair, and left in place for 30 minutes. After rinsing with water, the rare earth salt composition (A) is applied and left in place for 10 minutes. After rinsing, shampooing and then drying, the hair is dyed uniformly a pearly grey.

We claim:

1. Process for dyeing keratinous fibers comprising applying to said fibers:
   (a) a component (A) containing at least one rare earth salt in a medium suitable for dyeing said fibers, and
   (b) a component (B) containing, in a medium suitable for dyeing said fibers, at least one indole derivative having formula (I):

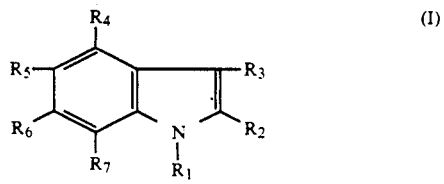

wherein
$R_1$ represents hydrogen or $C_1$-$C_4$ alkyl,
$R_2$ and $R_3$, each independently, represent hydrogen, $C_1$-$C_4$ alkyl, carboxyl or ($C_1$-$C_4$ alkoxy) carbonyl,
$R_4$, $R_5$, $R_6$ and $R_7$, each independently represent hydrogen; $C_1$-$C_4$ alkyl; carboxyl; $C_1$-$C_4$ carboxyalkyl; ($C_1$-$C_4$ alkoxy) carbonyl; ($C_1$-$C_4$ alkoxy) carbonyl ($C_1$-$C_4$ alkyl); carbamyl; halogen; mono- or polyhydroxy ($C_1$-$C_4$ alkyl); $C_1$-$C_4$ aminoalkyl; OZ wherein Z represents hydrogen or $C_1$-$C_{20}$ linear or branched alkyl; aryl ($C_1$-$C_4$ alkyl); formyl; linear or branched $C_2$-$C_{20}$ acyl; linear or branched $C_3$-$C_{20}$ alkenoyl; —SiR$_{11}$R$_{12}$R$_{13}$; —P(O)(OR$_8$)$_2$ or R$_8$OSO$_2$—,
or $R_4$ and $R_5$, or alternatively $R_5$ and $R_6$, or alternatively $R_6$ and $R_7$ form, together with the carbon atoms to which they are attached, a ring optionally containing a carbonyl group, a thiocarbonyl group, a >P(O)(OR$_8$) group or a >CR$_9$R$_{10}$ group,
with the proviso that at least one of $R_4$ to $R_7$ represents OZ or alternatively $R_4$ and $R_5$, or alternatively $R_5$ and $R_6$, or alternatively $R_6$ and $R_7$ form a ring,
$R_8$ and $R_9$ represent hydrogen or $C_1$-$C_4$ alkyl,
$R_{10}$ represents $C_1$-$C_4$ alkoxy or mono- or di ($C_1$-$C_4$ alkyl) amino, and
$R_{11}$, $R_{12}$ and $R_{13}$, each independently, represent linear or branched $C_1$-$C_4$ alkyl,
and the corresponding alkali metal salt, alkaline earth metal salt, ammonium salt, amine salt, addition salt of an inorganic acid or addition salt of an organic acid,
components (A) and (B) being applied on said fibers using a single composition, or component (A) being applied on said fibers prior or subsequent to the application of component (B),
said rare earth salt being present in an amount ranging from 0.1 to 8 percent by weight relative to the total weight of the composition applied to the fibers and said indole derivative being present in an amount ranging from 0.1 to 5 percent by weight relative to the total weight of said composition applied to the said fibers.

2. Process according to claim 1, wherein the component (B) contains 5,6-dihydroxyindole.

3. Process according to claim 1, wherein the component (B) contains at least one compound selected from the group consisting of 4-hydroxy-5-methoxyindole, 5-methoxy-6-hydroxyindole, 2,3-dimethyl-5,6-dihydroxyindole, 3-methyl-5,6-dihydroxyindole and 6-hydroxyindole.

4. Process according to claim 1, wherein, in a first stage, a composition consisting of the component (A) is applied, and in that, after an exposure time of 1 to 30 minutes, the composition consisting of the component (B), containing the indole derivative of formula (I) defined in claim 1, is applied.

5. Process according to claim 1, wherein the application of the two compositions (A) and (B) is followed by a treatment with hydrogen peroxide or with an inorganic or organic base.

6. Process according to claim 1, wherein the application of the components (A) and (B) is separated by a stage of rinsing of the treated fibres with water.

7. Process according to claim 1, wherein the rare earth salts are salts of lanthanides.

8. Process according to claim 1, wherein the rare earth salts are salts of cerium Ce$^{3+}$, Ce$^{4+}$; of lanthanum La$^{3+}$; of europium Eu$^{2+}$, Eu$^{3+}$; of gadolinium Gd$^{3+}$, of ytterbium Yb$^{2+}$, Yb$^{3+}$; and of dysprosium Dy$^{3+}$.

9. Process according to claim 1, wherein the rare earth salts are rare earth sulphates, chlorides and nitrates.

10. Process according to claim 1, wherein a composition (A) containing a salt, of cerium Ce$^{3+}$ or Ce$^{4+}$ in a medium suitable for dyeing having a pH of between 2 and 12 is applied on the fibres, and in that this application is followed or preceded by the application of a solution containing the indole derivative of formula (I) in a medium suitable for dyeing having a pH of between 7.5 and 12.

11. Process according to claim 10, wherein the application of the two compositions is followed by a treatment with a hydrogen peroxide solution having a pH of between 2 and 12, or by a treatment with an inorganic or organic base.

12. Process according to claim 11, comprising the application of a single composition containing the component (A) and the component (B) for an exposure time of between 1 and 30 minutes, and that rinsing with water is then performed.

13. Process according to claim 12, wherein the components (A) and (B) are mixed at the requisite time immediately before the dyeing of the fibres, and in that the application of the composition in effective amounts for dyeing the keratinous fibres is then performed.

14. Process according to claim 1, wherein the rare earth salt is a salt of cerium Ce$^{3+}$, europium Eu$^{2+}$ or the salt of ytterbium $Yb^{2+}$, in the form of a sulphate or chloride.

15. Process according to claim 1, wherein a single composition containing by way of component (A) a $Ce^{3+}$ sulphate or chloride, and by way of component (B) at least an indole derivative of the formula (I), having a pH of between 2 and 7, is applied on the fibres.

16. Process according to claim 15, wherein the application is followed by a treatment with hydrogen peroxide at a pH of between 2 and 12, or by a treatment with an inorganic or organic base.

17. Process according to claim 1, wherein human hair is dyed.

18. A composition for dyeing keratinous fibers comprising, in a medium suitable for dyeing said fibers, at least one rare earth salt and at least one indole derivative of formula (I):

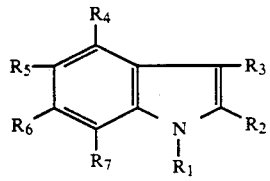

wherein
$R_1$ represents hydrogen or $C_1-C_4$ alkyl,
$R_2$ and $R_3$, each independently, represent hydrogen, $C_1-C_4$ alkyl, carboxyl or ($C_1-C_4$ alkoxy) carbonyl,
$R_4$, $R_5$, $R_6$ and $R_7$, each independently represent hydrogen; $C_1-C_4$ alkyl; carboxyl; $C_1-C_4$ carboxyalkyl; ($C_1-C_4$ alkoxy) carbonyl; ($C_1-C_4$ alkoxy) carbonyl ($C_1-C_4$ alkyl); carbamyl; halogen; mono-or polyhydroxy ($C_1-C_4$ alkyl); $C_1-C_4$ aminoalkyl; OZ wherein Z represent hydrogen or $C_1-C_{20}$ linear or branched alkyl; aryl ($C_1-C_4$ alkyl); formyl; linear or branched $C_2-C_{20}$ acyl; linear or branched $C_3-C_{20}$ alkenoyl; $-SiR_{11}R_{12}R_{13}$; $-P(O)(OR_8)_2$ or $R_8OSO_2-$,
or $R_4$ and $R_5$, or alternatively $R_5$ and $R_6$, or alternatively $R_6$ and $R_7$ form, together with the carbon atoms to which they are attached, a ring optionally containing a carbonyl group, a thiocarbonyl group, a $>P(O)(OR_8)$ group or a $>CR_9R_{10}$ group,
with the proviso that at least one of $R_4$ to $R_7$ represents OZ or alternatively $R_4$ and $R_5$, or alternatively $R_5$ and $R_6$, or alternatively $R_6$ and $R_7$ form a ring,
$R_8$ and $R_9$ represent hydrogen or $C_1-C_4$ alkyl,
$R_{10}$ represents $C_1-C_4$ alkoxy or mono- or di ($C_1-C_4$ alkyl) amino, and
$R_{11}$, $R_{12}$ and $R_{13}$, each independently, represent linear or branched $C_1-C_4$ alkyl,
and the corresponding alkali metal salt, alkaline earth metal salt, ammonium salt, amine salt, addition salt of an inorganic acid or addition salt or an organic acid,
said rare earth salt being present in an amount ranging from 0.1 to 8 percent by weight relative to the total weight of said composition applied to the fibers and said indole derivative being present in an amount ranging from 0.1 to 5 percent by weight relative to the total weight of said composition applied to said fibers.

19. The composition of claim 18 wherein said indole derivative is present in an amount ranging from 0.1 to 3 percent by weight based on the total weight of said composition applied to said fibers.

20. Composition according to claim 18, wherein the indole derivative is 5,6-dihydroxyindole.

21. Composition according to claim 18, wherein the indole derivative is chosen from 4-hydroxy-5-methoxyindole, 5-methoxy-6hydroxyindole, 2,3-dimethyl-5,6-dihydroxyindole, 3-methyl-5,6-dihydroxyindole and 6-hydroxyindole.

22. Composition according to claim 18, wherein the medium suitable for dyeing consists of an aqueous medium composed of water or a water/organic solvent mixture.

23. Composition according to claim 18, wherein the medium suitable for dyeing consists of essentially anhydrous solvent medium.

24. Composition according to claim 18, wherein the solvents are chosen from ethyl alcohol, propyl or isopropyl alcohol, tert-butyl alcohol, ethylene glycol, propylene glycol, ethylene glycol monomethyl, monoethyl and monobutyl ethers, propylene glycol and dipropylene glycol monomethyl ethers, and methyl lactate.

25. Composition according to claim 18, packaged in a closed vessel essentially free from oxygen and in the presence of a non-oxidizing inert gas.

26. Composition according to claim 18, packaged in an aerosol device in the presence of a propellent gas and a foam-generating agent.

27. Composition according to claim 18, containing one or more adjuvants chosen from fatty amides in proportions of 0.05 to 10%, anionic, cationic, nonionic or amphoteric surfactants or mixtures thereof, present in proportions of between 0.1 and 50%, thickening agents present in proportions of between 0.1 and 5%, perfumes, sequestering agents, film-forming agents, dispersants, conditioners, preservatives, opacifiers and agents for swelling keratinous fibres.

28. A multi-compartment device or kit for use in dyeing keratinous fibers comprising in a first compartment, a component (A) containing at least one rare earth salt in a medium suitable for dyeing said fibers; and in a second compartment, a component (B) containing, in a medium suitable for dyeing said fibers, at least one indole derivative of formula (I):

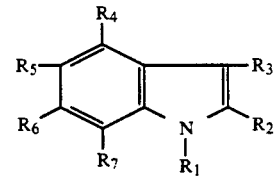

wherein
$R_1$ represents hydrogen or $C_1-C_4$ alkyl,
$R_2$ and $R_3$, each independently, represent hydrogen, $C_1-C_4$ alkyl, carboxyl or ($C_1-C_4$ alkoxy) carbonyl,
$R_4$, $R_5$, $R_6$ and $R_7$, each independently represent hydrogen; $C_1-C_4$ alkyl; carboxyl; $C_1-C_4$ carboxyalkyl; ($C_1-C_4$ alkoxy) carbonyl; ($C_1-C_4$ alkoxy) carbonyl ($C_1-C_4$ alkyl); carbamyl; halogen; mono-or polyhydroxy ($C_1-C_4$ alkyl); $C_1-C_4$ aminoalkyl; OZ wherein Z represent hydrogen or $C_1-C_{20}$ linear or branched alkyl; aryl ($C_1-C_4$ alkyl); formyl; linear or branched $C_2-C_{20}$ acyl; linear or branched $C_3$-$C_{20}$ alkenoyl; —$SiR_{11}R_{12}R_{13}$; —$P(O)(OR_8)_2$ or $R_8OSO_2$—, or $R_4$ and $R_5$, or alternatively $R_5$ and $R_6$, or alternatively $R_6$ and $R_7$ form, together with the carbon atoms to which they are attached, a ring optionally containing a carbonyl group, a thiocarbonyl group, a $P(O)(OR_8)$ group or a $CR_9R_{10}$ group, with the proviso that at least one of $R_4$ to $R_7$ represents OZ or alternatively $R_4$ and $R_5$, or alternatively $R_5$ and $R_6$, or alternatively $R_6$ and $R_7$ form a ring, $R_8$ and $R_9$ represent hydrogen or $C_1$-$C_4$ alkyl, $R_{10}$ represents $C_1$-$C_4$ alkoxy or mono- or di ($C_1$-$C_4$ alkyl) amino, and $R_{11}$, $R_{12}$ and $R_{13}$, each independently, represent linear or branched $C_1$-$C_4$ alkyl, and the corresponding alkali metal salt, alkaline earth metal salt, ammonium salt, amine salt, addition salt of an inorganic acid or addition salt or an organic acid, said rare earth salt being present in an amount ranging from 0.1 to 8 percent by weight relative to the total weight of said composition applied to the fibers and said indole derivative being present in an amount ranging from 0.1 to 5 percent by weight relative to the total weight of said composition applied to said fibers.

29. Device according to claim 28, comprising a third compartment containing an aqueous medium suitable for dyeing and intended for mixing with the contents of the second compartment when the medium suitable for dyeing in the composition present in this second compartment is anhydrous.

* * * * *